United States Patent [19]

Sato

[11] 4,296,243
[45] Oct. 20, 1981

[54] PROCESS FOR PRODUCING SORBIC ACID OR ITS DERIVATIVES

[75] Inventor: Kazuo Sato, Arai, Japan

[73] Assignee: Daicel Ltd., Osaka, Japan

[21] Appl. No.: 61,780

[22] Filed: Jul. 27, 1979

[30] Foreign Application Priority Data

Aug. 3, 1978 [JP] Japan .................................. 53-95186

[51] Int. Cl.$^3$ ...................... C07C 51/09; C07C 57/10; C07C 67/08; C07C 69/587
[52] U.S. Cl. .................................... 560/210; 560/183; 560/211; 560/212; 560/216; 562/599; 562/600; 562/601
[58] Field of Search ................ 562/601, 599; 560/216, 560/210, 212, 183, 211

[56] References Cited

U.S. PATENT DOCUMENTS

| | | | |
|---|---|---|---|
| 3,022,342 | 2/1962 | Fernholz et al. | 562/601 |
| 3,461,158 | 8/1969 | Hornig et al. | 562/601 |
| 3,845,118 | 10/1974 | Hey et al. | 562/601 |

*Primary Examiner*—Vivian Garner
*Attorney, Agent, or Firm*—Sughrue, Mion, Zinn, Macpeak & Seas

[57] ABSTRACT

A process for producing sorbic acid and its derivatives, which comprises reacting crotonaldehyde with ketene in the presence of a catalyst and decomposing or hydrolyzing the resulting adduct, said catalyst comprising a zinc salt of an aliphatic carboxylic acid and a phosphine or a pyridine.

7 Claims, No Drawings

PROCESS FOR PRODUCING SORBIC ACID OR ITS DERIVATIVES

BACKGROUND OF THE INVENTION

1. Field of the Invention

This invention relates to a process for producing sorbic acid and its derivatives (e.g., sorbic acid salts, sorbic acid esters, etc.). More particularly, the invention pertains to the use of a novel catalyst in the production of a crotonaldehyde-ketene adduct (an intermediate of sorbic acid to be referred to simply as a polyester) from crotonaldehyde and ketene.

2. Description of the Prior Art

Sorbic acid and its derivatives are characterized by a superior fungicidal activity and non-toxicity to man and are useful as food additives.

One typical method for the commercial production of sorbic acid comprises reacting crotonaldehyde with ketene in the presence of a catalyst and distilling off the unreacted crotonaldehyde or solvent from the reaction product to form a polyester (to be referred to as the synthesizing step), hydrolyzing the polyester in the presence of a mineral acid or an alkali hydroxide or heat-decomposing it in the presence of a catalyst to form crude sorbic acid (to be referred to as the decomposition step), and purifying the crude sorbic acid by distillation, adsorption, crystallization, etc., to form purified sorbic acid (to be referred to as the purification step).

Generally, improvement of a certain method is done by a completely remedial method or a coping method. Certainly, the former is a better measure, and this is true also with the production of sorbic acid. Usually, a method for producing sorbic acid is evaluated by the yield and purity (as shown by the degree of whiteness, etc.) of the resulting sorbic acid. Improvement of these factors is effected by improving the step of synthesizing the polyester, the source of sorbic acid. It is desirable to produce a polyester of better grade (as reflected by purity, etc.) in a higher yield. This is because from the standpoint of the overall process of producing sorbic acid, the purity of the polyester determines the portion of the polyester which is convertible to sorbic acid, and better purities naturally lead to higher yields of sorbic acid. The balance obtained by subtracting the purity of the polyester from 100% is that portion of the polyester which is not convertible to sorbic acid. This portion often becomes tarry at the time of decomposition or hydrolysis of the polyester, and reduces the grade of the resulting sorbic acid. As a result, an increased load is exerted on the subsequent purification step for the production of sorbic acid of a higher grade. This gives rise to an increase in the loss of sorbic acid incident to purification, and consequently reduces the yield of sorbic acid, resulting in a vicious circle. Thus, poor purities of the polyester result in poor yields and grades of sorbic acid.

Conventionally known catalysts used in the addition reaction of crotonaldehyde with ketene in the synthesizing step include, for example, Lewis acids such as boron fluoride and aluminum chloride (see U.S. Pat. No. 2,484,067), zinc salts of organic acids containing not more than 3 carbon atoms (see French Pat. No. 1,309,051), metal salts of fatty acids containing 4 to 18 carbon atoms (see Japanese Patent Publication No. 7212/62), and zinc sorbate (see British Pat. No. 885,217). However, the Lewis acids do not give results which are feasible in practical applications. Testing of the fatty acid metal salts has shown that the yield and purity of the polyester in the synthesizing step are low. Furthermore, in the decomposition and purification steps, the yield and whiteness of sorbic acid are poor, and by-product tarry materials occur in large amounts. In other words, the portion of the polyester which is convertible to sorbic acid, which corresponds to the purity of the polyester, is small. To put it another way, the yield and grade of the resulting sorbic acid are reduced because the portion of the polyester which is not convertible to sorbic acid is large.

SUMMARY OF THE INVENTION

Accordingly, a principal object of the present invention is to provide a process for producing sorbic acid from a better grade adduct of crotonaldehyde and ketene.

A more particular object of the present invention is to provide a process for preparing sorbic acid from an adduct which has a low tarry portion.

A further object of the present invention is to provide a process for producing sorbic acid having low colored matter.

Extensive investigations have led to the discovery that when a phosphine or a pyridine is used in addition to a zinc salt of an aliphatic carboxylic acid as a catalyst in the production of the polyester in the synthesizing step, the grade of the resulting polyester can be improved markedly, and, as a result, the yield and grade of sorbic acid in the subsequent decomposition and purification steps increase remarkably, and moreover, the resulting sorbic acid has a low content of colored matter and thus decreases the load on the subsequent purification step. Thus, the present invention provides a markedly improved process for producing sorbic acid and its derivatives over the conventional processes.

Thus, according to this invention, there is provided a process for producing sorbic acid and its derivatives, which comprises reacting crotonaldehyde with ketene in the presence of a catalyst, and decomposing or hydrolyzing the resulting adduct, said catalyst comprising a zinc salt of an aliphatic carboxylic acid and a phosphine or a pyridine.

DETAILED DESCRIPTION OF THE INVENTION

The zinc salt of aliphatic carboxylic acid used in this invention may be a salt containing water of crystallization or an anhydrous salt. The aliphatic carboxylic acid is a saturated or unsaturated aliphatic carboxylic acid having at least 2 but up to 18 carbon atoms and preferably 2 to 6 carbon atoms. Suitable aliphatic carboxylic acids include acetic acid, propionic acid, butyric acid, valeric acid, sorbic acid, stearic acid, etc.

Suitable phosphines are tertiary phosphines of the general formula $R_1R_2R_3P$, in which each of $R_1$, $R_2$ and $R_3$ represents an alkyl or aryl group. The alkyl group may be a straight chain, branched chain or cyclic alkyl group having 1 to 8 carbon atoms. The aryl group includes a phenyl group, an alkyl-substituted phenyl group (such as a tolyl group) and a halogen-substituted phenyl group (such as a p-chlorophenyl group). Specific examples of the tertiary phosphines are triethylphosphine, tripropylphosphine, tributylphosphine, triphenylphosphine, dimethylphenylphosphine and methyldiphenylphosphine.

Suitable pyridines are those expressed by the formula

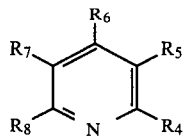

wherein each of $R_4$, $R_5$, $R_6$, $R_7$ and $R_8$ represents a hydrogen atom or a lower alkyl group (preferably a straight chain or branched chain alkyl group having 1 to 4 carbon atoms). Specific examples of these pyridines are pyridine, picoline, lutidine, gamma-collidine, tetramethylpyridine, pentamethylpyridine, methylethylpyridine, ethylpyridine, propylpyridine, butylpyridine, etc. A mixture of the phosphine and the pyridine cannot be used, but two or more of pyridines or phosphines can be used together.

The zinc salt of an aliphatic carboxylic acid as a catalyst component is added in an amount required to maintain the catalytic activity depending on the reaction temperature or the solubility of the zinc salt in the solvent used. Usually, the amount of the zinc carboxylate is about 0.1 to 5.0% and preferably about 0.2 to 4.0% by weight based on the crotonaldehyde. A suitable amount of the phosphine, the other catalyst component, is about 0.3 to 1.0 mol and preferably about 0.4 to 1.0 mol per mol of the zinc salt of the aliphatic carboxylic acid, and a suitable amount of the pyridine is about 0.5 to 3.0 mols and preferably about 1.0 to 2.5 mols per mol of the zinc salt of the aliphatic carboxylic acid.

The addition of the catalyst does not require a particularly complex operation, and the aliphatic carboxylic acid zinc salt and the phosphine or pyridine may be added successively or simultaneously. Preferably, the reaction is started after the mixture of the added components is stirred for about 30 minutes. Mixing of the aliphatic carboxylic acid zinc salt and the phosphine or pyridine possibly results in the formation of a complex between these components, forming a catalytically active species in the process of this invention. Hence, a separately prepared complex between the aliphatic carboxylic acid zinc salt and the phosphine or pyridine may be used as a catalyst ingredient.

The process of this invention is practiced by contacting liquid crotonaldehyde with gaseous ketene either batchwise or continuously. The ketene can be used at atmospheric pressure or at higher or lower pressures depending upon the mode of generation. It is also possible at this time to dissolve the catalyst in crotonaldehyde as a solvent and react the solution with ketene in a molar proportion less than the crotonaldehyde. Alternatively, in carrying out the reaction the catalyst may be diluted with another solvent such as an aromatic hydrocarbon (e.g., benzene, toluene, xylene, chlorobenzene, nitrobenzene, etc.); an aliphatic hydrocarbon (e.g., n-hexane, heptane, octane, etc.); a chlorinated hydrocarbon (e.g., chloromethylene, chloroform, carbon tetrachloride, etc.); or an alicyclic hydrocarbon (e.g., cyclohexane, cycloheptane, etc.). The reaction temperature should be determined by considering the boiling point of the solvent. Usually, the suitable reaction temperature is from about 0° to 60° C. Removal of the excess of crotonaldehyde or solvent by distillation from the resulting reaction mixture gives the polyester.

When the polyester is heat-decomposed in a customary manner in the presence of an alkali catalyst such as potassium carbonate or sodium acetate, or hydrolyzed in a customary manner with a strong acid such as hydrochloric acid, sulfuric acid, p-toluenesulfonic acid, etc. or a strong alkali such as an alkali hydroxide (e.g., NaOH, KOH, etc.), sorbic acid or sorbic acid salts are formed. When this procedure is performed in the presence of an alcohol, a sorbic acid ester can be directly obtained.

As a specific embodiment of the present invention, hydrolysis of the polyester with hydrochloric acid is shown below.

The suitable weight ratio of the polyester to hydrochloric acid is from 1:1 to 1:3, and the suitable hydrochloric acid concentration in its aqueous solution is at least 30% (i.e., concentrated hydrochloric acid). The hydrolysis temperature is chosen from the range of 50° to 120° C. When the resulting mixture is treated by filter or centrifuge, crude sorbic acid is obtained. To obtain purified sorbic acid, the crude sorbic acid is treated in a known manner such as distillation, adsorption or crystallization.

The process of this invention affords high purity polyester in high yields. Sorbic acid of high grade can be obtained in high yields by decomposing and then purifying the polyester. Since the resulting polyester has a very reduced content of by-product tarry materials as compared with polyesters obtained by the conventional processes, the color of the resulting sorbic acid is markedly improved, and therefore, the subsequent purification step can be performed advantageously.

In the purification step subsequent to decomposition, the reduced content of by-product tarry materials means a marked decrease in the load on conventionally practiced purifying operations such as distillation, adsorption (including ion exchange treatment and activated carbon treatment), recrystallization, and washing. Specifically, in the distillation method, the rectifying effect can be small (i.e., the impurities to be removed are small), the diameter and the number of trays in the distillation tower can be reduced, and moreover, the amount of heat energy consumed decreased. In the adsorption method, the volume of the apparatus can be reduced, and the amount of the adsorbent can also be decreased. In the recrystallization method or the washing method, the amount of the solvent used decreases, and the number of treating cycles can be reduced. Furthermore, the amounts of required subsidiary materials used decrease, and the cost of recovering them also decreases. With the reduced load on these operations the change of sorbic acid to a tarry material with time can also be inhibited. Thus, the industrial value of the process of the invention is very great.

The following Examples and Comparative Examples illustrate the present invention in greater detail. All parts in these Examples are by weight.

EXAMPLE 1

2 parts of zinc isobutyrate was added to 600 parts of crotonaldehyde, and 1 part of tri-n-butyl phosphine was added thereto. The mixture was stirred at room temperature for 30 minutes, and 179 parts of gaseous ketene was introduced into the mixture. During this time, the reaction mixture was maintained at 40° to 50° C. After the reaction, the unreacted crotonaldehyde was distilled off at a reduced pressure of 50 mmHg to afford 473 parts of a clear pale yellow polyester having a high viscosity. The apparent yield of the polyester based on the ketene was 99.1%. The molecular weight of the resulting polyester, measured by a vapor pressure osmometer, was 4,300 on an average.

100 parts of concentrated hydrochloric acid was added to 67.5 parts of the resulting polyester. The mixture was heated to 80° C. to hydrolyze the polyester. After cooling, the product was treated by a centrifugal separator to obtain crude sorbic acid. The crude product had a reduced content of by-product tarry matter. The crude sorbic acid was decolorized with activated carbon, and crystallized from an aqueous solution to afford 57.5 parts of sorbic acid having a melting point of 134° C. The yield of sorbic acid based on the polyester was 85.2%. The apparent purity of the polyester is evaluated by the yield of sorbic acid based on the polyester. To evaluate the whiteness of the resulting sorbic acid, 1 g of the sorbic acid was dissolved in a 1 N sodium hydroxide solution and the total amount was adjusted to 10 ml. The transmittance of this solution was measured at a wavelength of 400 m$\mu$ using a 1 cm cell with a 1 N sodium hydroxide solution as a control. The transmittance was 89.0%.

COMPARATIVE EXAMPLE 1

Instead of the zinc isobutyrate and tri-n-butyl phosphine, 2 parts of zinc isobutyrate alone was added to 600 parts of crotonaldehyde. With stirring, 179 parts of gaseous ketene was introduced. During this time, the reaction temperature was maintained at 40° to 50° C. After the reaction, the reaction mixture was worked up in the same way as in Example 1. The apparent yield of the polyester based on the ketene was 89.6%. The polyester had a clear yellow color, and a molecular weight of 2,100. The yield of sorbic acid obtained from the polyester was 76.9%. The transmittance of the sorbic acid solution was 71.0%, and the amount of by-product tarry matter was large.

EXAMPLE 2

Example 1 was repeated using 2 parts of zinc acetate and 1 part of tri-n-butyl phosphine instead of the zinc isobutyrate and tri-n-butylphosphine used in Example 1. The yield of the resulting polyester based on the ketene was 99.6%. The color of the polyester was clear pale yellow. The yield of sorbic acid obtained from the polyester was 84.8%. The transmittance of the sorbic acid solution was 87.5, and the amount of by-product tarry matter was small.

COMPARATIVE EXAMPLE 2

Example 2 was repeated using 2 parts of zinc acetate alone instead of the zinc acetate and tri-n-butylphosphine used in Example 2. The yield of the polyester based on the ketene was 89.1%, and the color of the polyester was brown. The yield of sorbic acid obtained from the polyester was 78.4%. The transmittance of the sorbic acid solution was 74.0%, and the amount of by-product tarry matter was large.

EXAMPLE 3

Example 1 was repeated using 2 parts of zinc isobutyrate and 1 part of triphenylphosphine instead of the zinc isobutyrate and tri-n-butylphosphine used in Example 1. The yield of the polyester based on the ketene was 98.9%, and the yield of sorbic acid obtained from the polyester was 84.2%. The transmittance of the sorbic acid solution was 86.8%.

EXAMPLE 4

Example 1 was repeated using 2 parts of zinc isobutyrate and 1.4 parts of pyridine instead of the zinc isobutyrate and tri-n-butylphosphine used in Example 1. The yield of the polyester based on the ketene was 99.1%, and the yield of sorbic acid obtained from the polyester was 84.0%. The transmittance of the sorbic acid solution was 88.0%.

EXAMPLE 5

Example 1 was repeated using 2 parts of zinc isobutyrate and 1.7 parts of $\alpha$-picoline instead of the zinc isobutyrate and tri-n-butylphosphine used in Example 1. The yield of the polyester based on the ketene was 99.5%. The yield of sorbic acid obtained from the polyester was 85.5%. The transmittance of the sorbic acid solution was 88.5%.

EXAMPLE 6

Example 1 was repeated using 2 parts of zinc acetate and 1.9 parts of 2,5-lutidine instead of the zinc isobutyrate and tri-n-butylphosphine used in Example 1. The yield of the polyester based on the ketene was 99.8%, and the yield of sorbic acid obtained from the polyester was 86.0%. The transmittance of the sorbic acid solution was 89.5%.

EXAMPLE 7

Example 1 was repeated using 2 parts of zinc acetate and 1.9 parts of 2,4-lutidine instead of the zinc isobutyrate and tri-n-butylphosphine used in Example 1. The yield of the polyester based on the ketene was 99.7%, and the yield of sorbic acid obtained from the polyester was 85.8%. The transmittance of the sorbic acid solution was 88.5%.

EXAMPLE 8

Ethanol (300 parts) and 3 parts of concentrated sulfuric acid as a catalyst were added to 100 parts of the polyester obtained in Example 1, and the mixture was reacted under reflux for 1 hour, followed by distillation at a reduced pressure of 10 mmHg to afford 109 parts of ethyl sorbate. The yield of the ethyl sorbate based on the polyester was 87.5%.

While the invention has been described in detail and with reference to specific embodiments thereof, it will be apparent to one skilled in the art that various changes and modifications can be made therein without departing from the spirit and scope thereof.

What is claimed is:

1. In a process for producing sorbic acid and its alkali salts and ester derivatives by reacting crotonaldehyde with ketene in the presence of a catalyst to form a polyester and heat-decomposing or hydrolyzing the resulting polyester addition product, the improvement wherein the catalyst in the polyester synthesizing step comprises a zinc salt of an aliphatic carboxylic acid and only one of a phosphine or a pyridine, wherein said carboxylic acid is a saturated or unsaturated carboxylic acid having at least 2 carbon atoms, said phosphine is represented by the formula $R_1R_2R_3P$ in which each of $R_1$, $R_2$ and $R_3$ represents an alkyl or aryl group, and said pyridine is represented by the formula:

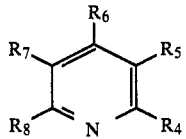

in which each of $R_4$, $R_5$, $R_6$, $R_7$ and $R_8$ represents a hydrogen atom or a lower alkyl group and wherein the amount of the zinc salt of the aliphatic carboxylic acid is about 0.1 to 5.0% by weight based on the crotonaldehyde, the amount of the phosphine is about 0.3 to 1.0 mol per mol of the zinc salt of the aliphatic carboxylic acid and the amount of the pyridine is about 0.5 to 3.0 mols per mol of the zinc salt of the aliphatic carboxylic acid.

2. The process of claim 1, wherein the crotonaldehyde and ketene are reacted at a temperature from about 0° to 60° C.

3. The process of claim 1, wherein in the polyester synthesizing step, crotonaldehyde or an inert solvent is used as a solvent.

4. The process of claim 1, wherein the amount of the zinc salt of the aliphatic carboxylic acid is about 0.2 to 4.0% by weight based on the crotonaldehyde, the amount of the phosphine is about 0.4 to 1.0 mol per mol of the zinc salt of the aliphatic carboxylic acid, and the amount of the pyridine is about 1.0 to 2.5 mols per mol of the zinc salt of the aliphatic carboxylic acid.

5. The process of claim 1, wherein the carboxylic acid is acetic acid, propionic acid, butyric acid, valeric acid, sorbic acid or stearic acid.

6. The process of claim 1, wherein the phosphine is triethyl phosphine, tripropyl phosphine, tributyl phosphine, triphenyl phosphine, dimethylphenyl phosphine, or methyldiphenyl phosphine.

7. The process of claim 1, wherein the pyridine is pyridine, picoline, lutidine, gamma-collidine, tetramethylpyridine, pentamethylpyridine, methylethylpyridine, propylpyridine, or butylpyridine.

* * * * *